United States Patent [19]

Varga

[11] Patent Number: 4,594,553
[45] Date of Patent: Jun. 10, 1986

[54] WATER PURITY MEASUREMENT

[75] Inventor: Istvan K. Varga, Windsor Gardens, Australia

[73] Assignee: The Commonwealth of Australia, Canberra, Australia

[21] Appl. No.: 719,047

[22] PCT Filed: Sep. 4, 1981

[86] PCT No.: PCT/AU81/00127

§ 371 Date: May 10, 1982

§ 102(e) Date: May 10, 1982

[87] PCT Pub. No.: WO82/01071

PCT Pub. Date: Apr. 1, 1982

Related U.S. Application Data

[63] Continuation of Ser. No. 380,674, May 10, 1982, abandoned.

[30] Foreign Application Priority Data

Sep. 12, 1980 [AU] Australia .............................. PE5552

[51] Int. Cl.$^4$ .............................................. G01N 27/60
[52] U.S. Cl. ..................................... 324/454; 324/453; 324/450
[58] Field of Search ............... 324/115, 376, 435, 444, 324/449, 450, 452, 457, 65 R, 454, 448, 453; 73/61.1 R; 204/400, 409; 210/900

[56] References Cited

U.S. PATENT DOCUMENTS

| 1,132,322 | 3/1915 | Fiego | 324/115 |
| 2,258,045 | 10/1941 | Christie | 324/448 |
| 2,315,805 | 4/1943 | Mayo et al. | 324/453 |
| 3,296,113 | 1/1967 | Hansen | 324/425 |
| 3,306,320 | 2/1967 | Bond | 324/453 |
| 3,368,144 | 2/1968 | Gerdes | 324/32 |
| 3,502,965 | 3/1970 | Gerdes et al. | 324/32 |
| 3,774,105 | 11/1973 | Henning et al. | 324/449 |

FOREIGN PATENT DOCUMENTS

| 1009721 | 11/1965 | United Kingdom | 324/449 |
| 1119393 | 7/1968 | United Kingdom | 324/449 |
| 1225800 | 3/1971 | United Kingdom | 324/450 |
| 2034902 | 6/1980 | United Kingdom | 324/454 |

Primary Examiner—Reinhard J. Eisenzopf
Assistant Examiner—Kevin D. O'Shea
Attorney, Agent, or Firm—Cushman, Darby & Cushman

[57] ABSTRACT

A method for measuring the purity of water in which the water is passed through an insulated pipe (1) in a cell spaced between electrodes (2-3) for measuring the tribo-electric electromotive force (e) generated by the flow, and wherein the resistivity of the water is calculated from the measured electromotive force.

9 Claims, 5 Drawing Figures

WATER PURITY MEASUREMENT

This is a continuation of application Ser. No. 380,674, filed May 10, 1982, which was abandoned upon the filing hereof.

This invention relates to the measurement of water purity, particularly where the purity is required to be measured in fractions of a part per million.

BACKGROUND

With the enormous expansion of activity in Semiconductor Technology over the last decade or so has come the need for chemicals of hitherto unheard of purity. We see reference to materials which typically have but purity levels measured in fractions of a part per million being used routinely in wet-way chemical processes on the silicon wafers. These materials are used in aqueous solutions, which in turn places a very considerable emphasis on the purity of the solvent, water. The present of traces of inorganic contaminants in both the chemicals being used and in the water can lead to the irreversible modification of the semiconductor materials during processing.

The normal technique to asses the purity of water is to measure the concentration of the contaminants in their ionised state using standard conductivity methods. This method, while being most satisfactory at normal impurity levels such as in tap water, distilled water, and the like, becomes extremely difficult when the water approaches the ultimate in chemical purity with resistivities of 10's of M$\Omega$cm, the level required in the semiconductor industry.

In the course of our research we have found that a tribo-electric e.m.f. which is generated due to friction in flowing water particularly when it is transported through insulating plastic pipes, can be used to measure water purity. In fact, this e.m.f. can cause damage to highly reflecting surfaces in water cooled pumping cavities in the solid laser. According to this invention use is made of this tribo-electric effect to measure the resistivity of the water, a function inversely of the ionic contamination and hence its purity, in a very simple measuring cell.

According to this invention the resistivity of water is measured by flowing water through a pipe of insulating material having linearly spaced electrodes, and measuring the tribo-electric e.m.f. generated by the flowing water, and calculating the resistivity of the water from this measurement.

In specific applications, such as the semiconductor technology referred to above, where generally the pipes are looped and the two ends are at the same potential, the invention is modified by having electrodes arranged to provide differing characteristics from adjacent sections of the cell so formed. This can be achieved by using materials of different characteristic or by having differing diameters in the cell to give a different velocity and hence achieve a different tribo-electric e.m.f.

While the invention has been based on the semiconductor industry, application of this effect could be widespread in many chemical plants and other industries.

Thus the invention can be applied as a method for measuring the purity of water which comprises flowing the water through a cell and measuring the tribo-electric e.m.f. generated by the flowing water, and calculating the resistivity of the water, the measuring of a tribo-electric e.m.f. being effected by flowing the water through a cell comprising a pipe of insulating material arranged between electrodes to which the measuring device is attached.

In the case where the two ends of the pipe are at a common potential, two dissimilar cell sections are preferably used which vary by wall characteristic, such as by using for instance a material known under the trade mark "Delrin" for one section of the cell and material known under the trade mark "Perspex" for the other section of the cell, arranged coextensive the one with the other with an end electrode at each end of the cell so formed and a further electrode between the two sections.

Instead of using two sections of the cell of dissimilar material the two sections can be of similar material but vary from each other by the internal diameter of the pipe sections.

DESCRIPTION OF PREFERRED EMBODIMENTS

Figure 1:
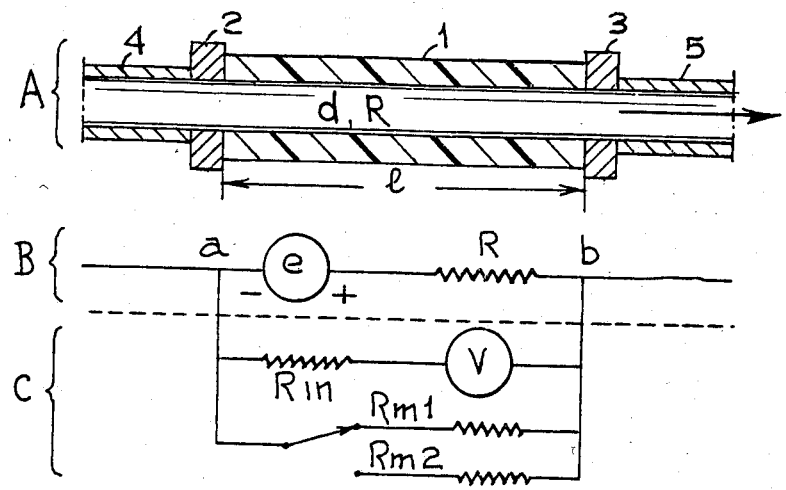
FIG. 1A is a schematic central section of a cell formed of a section insulating material having an electrode at each end, B showing the equivalent electrical circuit, and C the measuring circuit.
Figure 4:
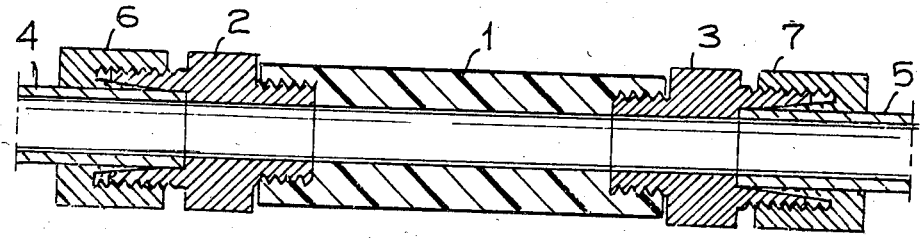
FIG. 4 is a central longitudinal section showing how the device of FIG. 1 can be constructed.

FIG. 1 shows a pipe section 1 of insulating material having electrodes 2 and 3 at the ends connected between pipes 4 and 5 through which the water flow occurs. As shown in FIG. 4 this can be constructed by threading the two ends of the plastic pipe section 1 and screwing to it a pair of electrodes 2 and 3 into which the ends of the pipes 4 and 5 project. Wedge nuts 6 and 7 lock the pipes 4 and 5 in position and effect a seal.

Figure 2:
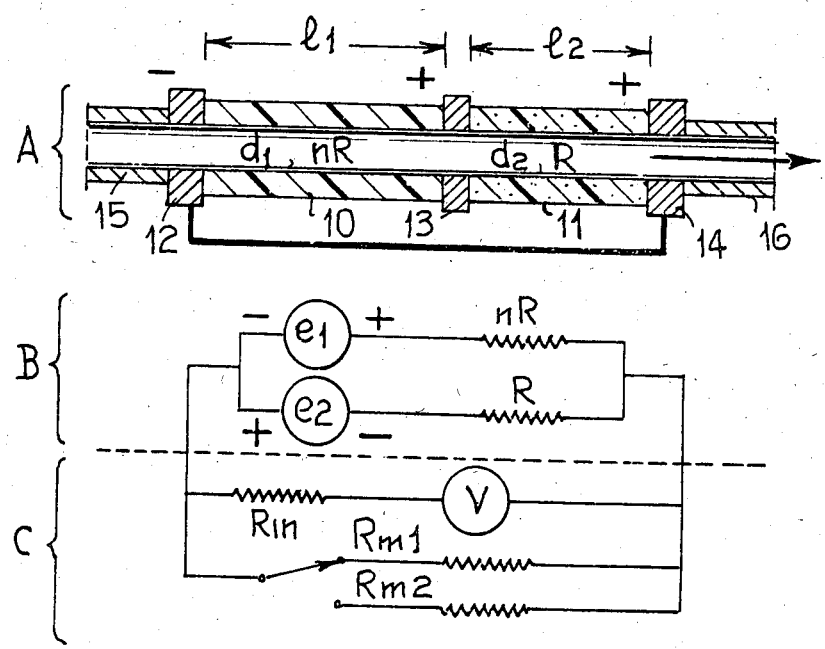
FIG. 2A is a similar view to FIG. 1A but showing the assembly used when the pipe is looped, in which case two insulating sections with electrodes at each end are used, B again showing the equivalent circuit, and C the measuring circuit of this type of cell.

The device of FIG. 2 has two pipe sections 10 and 11 of insulating material which differ in their physical characteristic using three electrodes 12, 13 and 14. Electrodes 12 and 14 are connected externally by an electrical short circuit, and the electrodes 12 and 14 are joined to the ends of the pipes 15 and 16. Readings are taken between electrode 13 and either electrode 12 or electrode 14. The readings taken between the center electrode 13 and either of electrodes 12 or 14 are achieved by connecting the measuring means (not shown in FIG. 2A) in the manner described in FIG. 2B. The actual construction of this can again be similar to the form illustrated in FIG. 4 excepting that a central electrode would be used, screwing into both of the pipe sections 10 and 15 of different insulating material.

Figure 3:
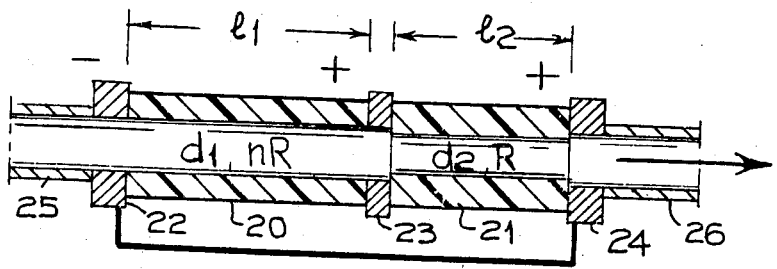
FIG. 3 is a further schematic view showing a cell with varying diameters as opposed to varying materials, the equivalent circuits being similar to B and C of FIG. 2.
Figure 5:
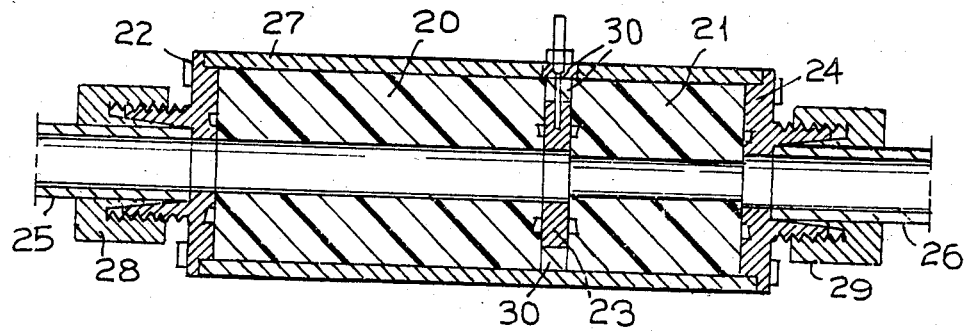
FIG. 5 is a view similar to FIG. 4 but showing construction of a cell as shown in FIG. 3.

The form illustrated in FIG. 3 uses pipe sections 20 and 21 of different dimension with electrodes 22, 23 and 24 and fitted between the ends of the pipes 25 and 26, could be similar to the form illustrated in FIG. 5, in which two end electrodes 22 and 24, joined by an external sleeve 27 and in which pipe sections 20 and 21 of similar insulating material are disposed with the central electrode 23 between them, the end electrodes 22 and 24 again having sockets to take the ends of the pipes 25 and 26 which are locked to the electrodes 22 and 24 by wedge nuts 28 and 29 which screw on to the electrodes 22 and 24. Insulation 30 isolates the central electrode from the sleeve 27.

The method of calculating the water purity is as follows:

Referring first to the simple cell of FIG. 1, the equivalent electrical circuit may be considered as shown in FIG. 1B and the measuring circuit FIG. 1C where e = generated voltage
R = Resistance of water column, function of $\rho$
l = the length,
d = the diameter of the cell
$R_{in}$ = voltmeter input resistance—tends to infinity and hence can be ignored
$R_{m1}$ $R_{m2}$ = Load resistors To obtain a value for R, the water resistance, two measurements are made using two resistors $R_{m1}$ and $R_{m2}$ giving two voltages $V_1$ and $V_2$ respectively.

R may then be derived from the following relation:

$$R = \frac{V_2 - V_1}{\frac{V_1}{R_{m1}} - \frac{V_2}{R_{m2}}}$$

If dissimilar plastics are used for the pipes or if the flow rates are modified in certain areas of the pipe by changing the diameter, then once again the e.m.f. can be measured.

When the cell is of dissimilar materials and uniform flow velocity, the two outer electrodes a and c are short circuited electrically and the measurement is made across b and c using the formula:

$$R = \frac{n+1}{n} \cdot \frac{V_2 - V_1}{\frac{V_1}{R_{m1}} - \frac{V_2}{R_{m2}}} \text{ where } n = \frac{l_1}{l_2}$$

When using similar materials but different diameters the measuring circuit of FIG. 2C applies and the formula from which R can be calculated is as follows:

$$R = \frac{n+1}{n} \cdot \frac{V_2 - V_1}{\frac{V_1}{R_{m1}} - \frac{V_2}{R_{m2}}}$$

$$\text{where } n = \frac{l_1}{l_2} \cdot \left(\frac{d_2}{d_1}\right)^2$$

From R the water resistivity, $\rho$ can be calculated as:

$$\rho = \frac{\pi d_2^2}{4 l_2} \cdot \left[\frac{V_2 - V_1}{\frac{V_1}{R_{m1}} - \frac{V_2}{R_{m2}}}\right]$$

Cells having an optimum of output voltage for a given system may be designed. A cell can be tailored by choice of cell length, diameter, and insulating materials.

Practical results have shown that a simple cell having the configuration as in FIG. 4 and inserted in a working system in which the system "loops" are very large and hence electrically isolated has worked extremely well.

Results of checks against a conventional conductivity cell system are shown in table 1. The tribo-electric cell was inserted in a working water treatment plant and the results calculated from the tribo-electric cell are shown against the readings given by the standard conductivity cell system.

| Conductivity Meter (m cm) | (MΩcm) By tribo-electric cell readings |
|---|---|
| 0.12 | 0.12 |
| 0.57 | 0.58 |
| 1.49 | 1.50 |
| 2.7 | 2.6 |
| No calibration on meter | 5.7 |
| No calibration on meter | 8.0 |
| No calibration on meter | 11.0 |

Tests on the more complex system, FIG. 5 confirm the theoretical tribo-electric model of the system. The voltages generated by the differences of cell insulating materials, differing diameters and differing cell lengths have been as predicted. Inner wall finish of the plastic tube does not appear to have any marked effect in the first instance on cell voltage; in our measurements any variations are lumped with the "tribo-electric" constant K for that particular cell. In all tests, it is assumed that flow-rates have been maintained constant for the period of the measurement, several seconds only.

Although various forms of the invention have been described in some detail it is to be realised that the invention is not to be limited thereto but can include various modifications falling within the spirit and scope of the invention.

I claim:

1. A device for measuring the purity of water which comprises a cell having at least a pipe in it arranged for water to be measured to flow therethrough, said pipe being formed of electrically insulating material and formed in two sections confined between a pair of spaced outer electrodes held together by a conductive sleeve engaging the said electrodes, said electrodes each having a socket to receive one end of a divided pipe line and each electrode having means to engage and hold the pipe line ends, further comprising a center electrode disposed between the two sections and insulated from the said sleeve and having an external electrical connection to each outer electrode and to a measuring means, which means comprises, a voltmeter and pair of alternately selectable parallel different value resistances of lower resistivity than the said voltmeter connected between said electrodes to measure the tribo-electric electro-motive force generated across the electrically insulating material under two different resistive loadings to calculate a resitivity figure indicating purity of the water.

2. A device according to claim 1 wherein the said cell has sections which differ by the nature of the insulating material from which each said section is formed, and an electrode between the said sections.

3. A device according to claim 1 wherein the said cell has sections which differ by the internal cross-sectional dimension of the sections, and an electrode between the said sections.

4. A device according to claim 1 wherein the said sections are of the same internal diameter for constant velocity flow therethrough and the said electrodes disposed at each end of the said pipe are connected together electrically and the said measuring means are connected between the said electrodes and a third electrode disposed between the said sections.

5. A device according to claim 1 wherein the said sections are of different internal diameter for different velocity flow therethrough and the said electrodes disposed at each end of the said pipe are connected together electrically and the said measuring means are connected between the said end electrodes and a third electrode between the said sections.

6. A device for measuring the purity of water which comprises a cell arranged for water to be measured to flow therethrough, said cell being formed of electrically insulating material, an electrode at each end of said cell, each said electrode having means to receive one end of a divided pipe line, each said electrode including means to sealably engage the said pipe line ends, means to hold the said pipe line ends to the electrode, and measuring means including a voltmeter and a pair of alternate selectable parallel different value resistances of lower resistivity than the said voltmeter connected between the said electrodes to measure the tribo-electric electromotive force generated across the electrically insulating material under two different resistive loadings to calculate a resistivity figure indicating purity of the water.

7. A method for measuring the purity of water, which comprises flowing water through a cell, wherein said cell is comprised of a single pipe section of insulating material disposed between electrodes arranged to measure the electromotive force generated by the water flowing through the cell, characterized by calculating the resistivity of the water from the tribo-electric electromotive force generated, the value of resistivity being indicative of the level of purity of the water, by connecting between the said electrodes a voltmeter of sufficiently high input resistance as to be ignored, and across it a pair of alternately selectable parallel different value resistances, $R_{m1}$ and $R_{m2}$, and by determining the resistivity $\rho$ of the water by the formula $$\rho = (\pi d^2/4l)[(V_2 - V_1)/[(V_1/R_{m1}) - (V_2/R_{m2})]]$$

wherein d is the internal diameter of the single pipe section, l is its length, and $V_1$ and $V_2$ are the tribo-electric voltages detected by the voltmeter when the resistances $R_{m1}$ and $R_{m2}$ respectively are switched in parallel with the voltmeter.

8. A method for measuring the purity of water, which comprises flowing water through a cell, wherein said cell is comprised of a pipe of insulating material disposed between electrodes arranged to measure the electromotive force generated by the water flowing through the cell, characterized in that the pipe comprises two pipe sections of the same insulating material and with different internal diameters producing different partial cell voltages by the tribo-electric effect, the pipe having a center electrode between the two pipe sections, the level of purity of the water being indicated by the value of the resitivity of the water, which is found by interconnecting the end electrodes electrically and connecting between the center electrode and the end electrodes a voltmeter of sufficiently high input resistance as to be ignored, and across it a pair of alternately selectable parallel different value resistances $R_{m1}$ and $R_{m2}$, and determining the resitivity, $\rho$, of the water by the formula $$\rho = (\pi d_2^2/4l_2)[(V_2 - V_1)/[(V_1/R_{m1}) - (V_2/R_{m2})]][(1+n)/n]$$

wherein $d_2$ and $l_2$ are the internal diameter and length of one pipe section, $V_1$ and $V_2$ are the tribo-electric voltages detected by the voltmeter when the resistances $R_{m1}$ and $R_{m2}$ respectively are switched in parallel with the voltmeter, and $$n = (l_2/l_2) \cdot (d_2/d_1)^2$$

wherein $l_1$ and $d_1$ are the length and internal diameter of the other pipe section.

9. A method for measuring the purity of water, which comprises flowing water through a cell in the form of a pipe of insulating material disposed between electrodes arranged to measure the tribo-electric electromotive force generated by the water flowing through the cell, characterized in that the pipe comprises two pipe sections with the same internal diameter and of insulating material having different characteristics producing different partial cell voltages by the tribo-electric effect, the pipe having a center electrode between the two pipe sections, the level of purity of the water being indicated by the value of the resistivity of the water, the resistivity being found by interconnecting the end electrodes electrically and connecting between the center electrode and the end electrodes a voltmeter of sufficiently high input resistance as to be ignored, and across it a pair of alternately selectable parallel different value resistances $R_{m1}$ and $R_{m2}$, and determining the resistivity $\rho$ of the water by the formula $$\rho = (\pi d_2^2/4l_2)[(V_2 - V_1)/[(V_1/R_{m1}) - (V_2/R_{m2})]][(-1+n)/n]$$

wherein $d_2$ and $l_2$ are the internal diameter and length of one pipe section, $V_1$ and $V_2$ are the tribo-electric voltages detected by the voltmeter when the resistances $R_{m1}$ and $R_{m2}$ respectively are switched in parallel with the voltmeter, and $n = l_1/l_2$ where $l_1$ is the length of the other pipe section.

* * * * *